Figure 1:
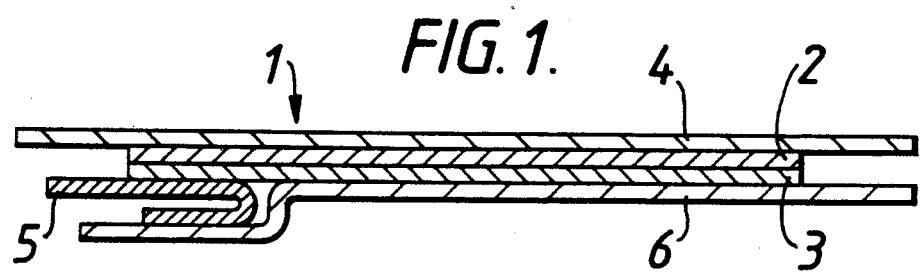

United States Patent [19]

Ward

[11] Patent Number: 5,000,172

[45] Date of Patent: Mar. 19, 1991

[54] DRESSING SYSTEM WITH REFERENCE MARKS

[75] Inventor: William J. Ward, Hull, United Kingdom

[73] Assignee: Smith & Nephew plc, United Kingdom

[21] Appl. No.: 345,987

[22] Filed: May 2, 1989

[30] Foreign Application Priority Data

May 5, 1988 [GB] United Kingdom ............... 8810572
Dec. 14, 1988 [GB] United Kingdom ............... 8829151

[51] Int. Cl.$^5$ .................. A61F 13/00; A61F 15/00; A61L 15/00
[52] U.S. Cl. ..................... 128/155; 604/307; 206/441; 128/888
[58] Field of Search ............. 128/155, 156, 888; 604/304, 307; 206/440, 441

[56] References Cited

U.S. PATENT DOCUMENTS

| | | | |
|---|---|---|---|
| 4,341,208 | 7/1982 | Gordon | 604/307 |
| 4,541,426 | 9/1985 | Webster | 128/156 |
| 4,600,001 | 7/1986 | Gilman | 128/156 |
| 4,753,232 | 6/1988 | Ward | 128/156 |
| 4,786,282 | 11/1988 | Wagle et al. | 128/156 |

Primary Examiner—Randall L. Green
Assistant Examiner—Paul Prebilic
Attorney, Agent, or Firm—Jacobs & Jacobs

[57] ABSTRACT

Wound dressing systems, comprising a transparent translucent dressing e.g. a pressure sensitive adhesive dressing, and at least one further transparent or translucent layer having reference marks which are capable of being used to monitor the wound. The translucent or transparent layer may form part of the dressing as applied to the wound or may be one of the protectors for the dressing, or may be removable support layer over the non-adhesive coated surface of the dressing.

16 Claims, 1 Drawing Sheet

DRESSING SYSTEM WITH REFERENCE MARKS

The present invention relates to a wound dressing system and in particular to a wound dressing system which includes a transparent or translucent layer having reference marks which are capable of being used to monitor the size of the wound.

The monitoring of the size of a wound during treatment can provide a guide to the progress of the wound. In the past, however, monitoring of the wound size has been difficult to achieve because available measuring instruments are laborious and difficult to use and can also contaminate the wound if unsterile. Furthermore the wound size results obtained with these instruments are often subjective. It would therefore be an advantage to provide a means for monitoring the size of a wound during treatment which did make use of conventional measuring instruments.

Adhesive dressings for application to a wound normally comprise an adhesive coated conformable backing layer such as a flexible film to render the dressings comfortable to wear. Desirably the flexible film should be relatively thin to render the dressing highly conformable. A highly conformable dressing of this type is known as OpSite (Trade mark, Smith and Nephew Associated Companies p.l.c.) OpSite dressings comprise a 25 to 30 μm thick film of polyurethane coated with a polyvinyl ether adhesive. Such dressings can provide a barrier to the liquid water and bacteria penetrating to the wound and are also sufficiently moisture vapor permeable to allow the dressing to be left in place on the wound for periods in excess of 24 hours without causing maceration of the skin. In addition these dressings advantageously are also sufficiently transparent or translucent to allow observation of the wound during healing. These dressings, however, do not have a means to readily monitor the progress or size of the wound during healing. A dressing arrangement has now been found which has such a means.

Accordingly the present invention provides a wound dressing system comprising a transparent or translucent dressing including at least one transparent or translucent layer having reference marks which are capable of being used to monitor the wound.

In accordance with a further embodiment of the invention there is provided a method of monitoring a wound e.g. changes in the size or topography covered with a transparent or translucent dressing, which method comprises superimposing a layer of transparent or translucent material bearing reference marks as indicative of wound dimensions, viewing the wound, during the period it is covered by the dressing, the layer and determining the change in size or topography of the wound.

The present invention further provides adhesive dressing comprising a backing layer having a pressure sensitive adhesive layer coated on one surface thereof, a removable protector covering the adhesive surface and extending beyond the backing layer at one or more edges thereof, and a support layer, removably attached to the non-adhesive coated surface of the backing layer and also extending beyond the backing layer to at least one of the same edges as the removable protector, in which the support layer is a transparent polymeric film carrying reference markings.

The dressings used in the invention may be adhesive dressings and thus will comprise a backing layer and an adhesive, for example pressure sensitive adhesive, layer coated on at least one side thereof, both of which are transparent or translucent. The adhesive may be coated over one entire surface of the backing layer or over part of it, e.g. around the periphery. Alternatively, the dressings may be non-adhesive ones.

By the term 'system' is meant not only the dressing per se but also includes components such as the protector layers for adhesive coatings, if present, overlayers, wrappers, information sheets, etc. all contained with the dressing package.

Preferably the dressing employed in the system comprises a thin flexible film to render the wound dressing thereof highly conformable.

A transparent or translucent layer when used herein means a layer which will allow observation of at least the general outline of the surface topography when viewed through the layer.

The transparent or translucent layer having the reference marks thus may be used to monitor the size of the wound by placing the layer directly over the wound or over another transparent or translucent layer covering the wound and measuring the size of the wound relative to the reference marks. The references marks may also be employed as a cutting for dressings wounds in awkward areas such as the elbow or heel.

The wound dressing system of the invention thus allows the size of a wound to be readily monitored. Such an arrangement therefore avoids the past problems encountered by the use of separate measuring instruments.

The wound dressing system preferably comprises a wound dressing assembly which includes at least one layer having reference marks. The layer having reference marks can be any of the layers of the wound dressing assembly of the invention providing that the layer is transparent or translucent. Since the wound dressings employed in the system of the invention may have a transparent or translucent backing and adhesive layer, the reference marks can be on the backing layer, which is preferably a thin film backing layer, or the adhesive layer.

The presentation of a further translucent or transparent layer, carrying reference marks a protector for an adhesive coated dressings or as a carrier for supporting the dressings offers further advantages in addition to being able to use the layer to monitor the healing of wounds. By incorporating the layer into the dressing structure, the reference marks may be used as guidelines for cutting the dressing, prior to application, so that it can be readily applied to awkward areas such as the elbow, knee or heel. This advantage is particularly apparent where the further layer is employed as a carrier for supporting a dressing, especially a thin film dressing since the dressing is supported, after any adhesive protectors have been removed during application to the wound. Once the dressing is in situ, the carrier is removed.

Reference marks on the transparent or translucent dressings used in the invention advantageously allow the size of a wound covered by the dressing to be monitored while the dressing remains in place.

Suitable backing film layers used in transparent or translucent adhesive dressings of the invention can be any of the thin transparent or translucent conformable backing film layers used on conventional adhesive dressings.

Preferred materials forming the dressing or the backing layers of adhesive dressings are elastomeric moisture vapor transmitting films.

Suitably the backing layer may comprise any of those materials which are conventionally employed to form thin film surgical dressings. Suitable materials include those described in United Kingdom Patent No. 1280631, European Patents No. 51935, 91800 and 178740.

Favored elastomeric moisture vapor transmitting films include those formed from polyether polyurethane, polyester polyurethane, hydrophilic polyurethane and polyester-polyether copolymers.

Suitable polyether polyurethanes are described in U.S. Pat. No. 2,899,411. Suitable polyester polyurethanes are described in U.S. Pat. No. 2,871,218. Apt polyester and polyether polyurethanes are known Estane (Trade Mark) available from B. F. Goodrich and in particular grades 5701, 5702, 5703, 5714F and 580201.

Other favored materials include hydrophilic polymers such as hydrophilic polyurethanes including those described in United Kingdom Patent No. 2093190B, especially the polyurethane described in Example 2 therein.

Suitable dressings for use in the dressing systems of the invention are disclosed in European Patent No. 91800.

Other apt materials are elastomeric polyether polyesters, for example those known as Hytrels (Trade Mark) and polyether polyamides, for example those known as Pebaxes (Trade Mark).

An apt polyester-polyether copolymer is known as Hytral 4056 available from Dupont.

Suitably the backing layer is moisture vapor permeable and has a moisture vapor transmission rate, of at least 500 $g/m^2/24$ h at 37° C. and 100% to 10% relative humidity difference, more suitably at least 1200 $g/m^2/24$ h and preferably at least 1600 $g/m^2/24$ h.

The thickness of the films used for the backing layer can be from 9 to 100 $\mu$m and can suitably be 9 to 80 $\mu$m. More suitably the backing layer is 15 to 50 $\mu$m thick and can preferably be 20 to 40 $\mu$m for example 27.5, 30 $\mu$m, 35 $\mu$m.

The adhesive used in the transparent or translucent adhesive dressings employed the invention can be any of the pressure sensitive adhesives used for coating conventional transparent or translucent wound dressings. Preferably are adhesives which form moisture vapor transmitting adhesive layers.

Aptly the pressure sensitive adhesive layer may be formed form an adhesive which is conventionally used for contact with the skin. Suitable adhesives include polyvinyl alkyl ether adhesive and acrylate ester copolymer adhesives. Suitable adhesives are described in United Kingdom Patent No. 1280631 and European Patents Nos. 35399 and 51935. Preferably the adhesive is a polyvinyl ethyl ether adhesive or an acrylate ester copolymer adhesive formed by the copolymerization of 2-ethylhexyl acrylate, butyl acrylate and acrylic acid.

Favored adhesives of this type are polyvinyl ether adhesives and acrylic adhesives. An apt acrylic adhesive comprising a copolymer of 47 parts by weight of butyl acrylate, 47 parts by weight of 2-ethylhexylacrylate and 6 parts by weight of acrylic is disclosed in United Kingdom Patent No. 2070631.

The adhesive can be coated as a continuous or discontinuous layer, for example, an all-net layer or a pattern spread layer. The layer may be a porous microporous or non-porous layer. Such adhesive coatings will generally have a coating weight per unit area of 10 to 75 $g/m^2$, more usually of 15 to 65 $g/m^2$ and will preferably have a weight per unit area of 20 to 40 $g/m^2$. In terms of thickness the adhesive layer may be from 15 to 65 $\mu$m thick, preferably from 20 to 40 $\mu$m thick.

The transparent or translucent layer having reference marks may be part of the dressing assembly of the invention which is removable prior to or after application of the dressing to the wound site. Such a layer can be used to monitor the size of the wound prior to application and after removal of the dressing from the wound as well as whilst the dressing is in situ. Since the dressing used in the invention is transparent or translucent, the layer may also be used to monitor the size of the wound during and/or after application of the dressing.

Thus the system of the invention can comprise transparent or translucent releasable protector over the adhesive surface of a dressing comprising, for example, a pressure sensitive adhesive coated transparent or translucent backing film wherein the reference marks are on the releasable protector.

The releasable protector can be a split protector for example as used in first aid dressing but it may extend substantially over the whole surface of the dressing.

The releasable protector used may be any of the transparent or translucent release protectors used on adhesive wound dressings. Suitable protectors include transparent or translucent plastics films made of a polyolefine such as polypropylene, polyethylene and copolymers thereof, polyamide and polyester, coated with a release agent such as a silicone resin. The reference marks, when present, are preferably on the non-release coated surface of the protector to allow further marking of the surface.

Once removed from the dressing in order for the dressing to be applied, the protector may be retained and need to monitor the wound through the dressing.

In a further embodiment of the invention the dressing comprises a transparent or translucent removable carrier member over the dressing or the non-adhesive coated surface of the backing layer of an adhesive dressing and the reference marks are on the carrier member.

The carrier member provides support for the backing layer during application of the dressing to the wound.

It has been found that a carrier member can significantly facilitate the application of highly conformable thin film adhesive dressings of the invention by inhibiting the puckering and creasing which normally occurs when these highly conformable dressings are applied to the skin. After application of the dressing to the wound the carrier member is removed from the backing layer. Suitably the support layer is formed from a paper or polymeric film. Preferably the carrier is a transparent or translucent film carrying reference marks. The reference marks on the carrier member used in the invention can thus be used to monitor the size and progress of the wound during and after application of a transparent or translucent dressing of the invention for example by marking the wound length or area on the outer surface of the carrier member. The marked carrier member can then be removed from the dressing and stored for example with the patents records for further reference or use.

The carrier member used in the invention can cover the whole or a part of the backing layer. It is preferred, however, that it covers the whole of the backing layer to provide an adequate area of reference marks for monitoring the size of the wound more preferably the support layer extends beyond the edges of the backing layer. Such a carrier member can be releasable attached for example by bonding, to the non-adhesive surface of backing layer. Carrier members or layers of this type are disclosed in European Patent Application No. 0051935.

Transparent or translucent carrier members may be made of material such as glassine paper, plastics film. In favored dressings of the invention the carrier member is plastics film.

Suitable plastics films,. of this type include those films made of an olefin homopolymer or copolymer such as polypropylene or polyethylene, polyamide, polyethylene terephthallate, polycarbonate and polystyrene.

The choice of material for the carrier member will be dictated on the one hand by factors such as the size and intended use of the final dressing and on materials having high flexural moduli such polycarbonates may be employed in the form of relatively thin films or strips whereas materials such as low density polyethylene will have to be employed as thicker sheets or strips. For example materials such as 50 $\mu$m low density and 30 $\mu$m high density polyethylene, 50 $\mu$m polypropylene and 25 $\mu$m translucent glassial paper sheets of a size 10 cm $\times$ 14 cm have sufficient flexural rigidity for use. Low density polyethylene film of a thickness of 225 $\mu$m may be used for larger size dressings.

The support layer may be attached to the backing layer by virtue of casting or extruding the backing layer onto the support layer thereby forming an attachment which is easily reversed. Suitably the support layer maybe formed from a transparent polymeric film such as polyethylene or polypropylene film or from an opaque silicone or polyethylene coated paper. Apt support layers comprise a laminate of polyolefins. Aptly the support layer is conformable by which it is meant that the support layer will conform to the contours of a surface to which it is applied. The support layer may be left attached to the backing layer without detracting seriously from the performance of the dressing, though it is preferred to remove the support layer. The support layer may carry markings including those in the form of a grid or concentric circles and the like whereby the progress of a healing wound or ulcer may be monitored. In this case the support layer remains on the backing layer.

In a preferred embodiment, a support layer is formed by first printing the reference markings, for example a grid pattern on an intermediate film such as one of polypropylene and thereafter laminating polyethylene films to both opposed surfaces of the printed polypropylene film, there "sandwiching" the printed substrate. The inks employed for printing the reference marks are those conventionally employed for over printing plastics materials and should be non-toxic. In a typical laminated support layer the printed polypropylene printed substrate will have a weight of about 55 gm m$^2$ and be laminated on both sides with polyethylene at a weight of about 20 gm m$^2$ per surface.

In an alternative embodiment the carrier member may be releasably attached to opposing edge margins of the backing layer so that the carrier member bridges the backing layer. Such a carrier member is not bonded to the backing layer over its entire surface and therefore does not prevent it conforming to the skin surface during application of the dressing to a wound.

The carrier member, or layer can be directly or indirectly attached to opposing edge margins of dressing.

In one form of this embodiment, the carrier member is directly attached to the opposing edge margins of the dressing. However, in another form the dressing has a removable handle attached to each of the opposing end margins and the carrier member is attached to each handle. The attachment of the carrier member to each handle may be releasable or permanent as will be explained hereinafter.

For small or medium size dressings that carrier member may be directly or indirectly attached to backing layer at opposing edge margins alone so that the carrier member bridges the remaining portion of the backing layer.

However, when the dressings are of a large size it may be desirable to attach the carrier to the backing layer at intermediate points, lines or areas to maintain the member adjacent to but not adhering to the backing layer.

Dressings in accordance with the invention can have a removable handle attached to at least one of an preferably to each of the opposing edge margins. The carrier member can be secured to such handles. Such handles can be in the form of a strip of flexible material such a coated paper or plastics film.

The handles can be attached either directly to the adhesive at opposed margins of the dressing indirectly by means of strips of adhesive tape which are preferably tearable to render the handles removable. Suitable dressings with removable handles of the type are disclosed in United Kingdom Patent Application No. 2157955. The handles can be adhered in a position in which they lie on top of the backing layer or preferably in a position where they lie alongside the backing layer.

The carrier member can be secured to the handle by crimping thereto, by locating the ends of the carrier in slots of recesses provided in the handles by bonding the carrier to the handles for example by heat sealing or adhesive or by locating the handles in slots or recesses in the carrier.

The carrier member is preferably adhered to each handle along a line or strip area.

The carrier member may extend beyond each of the handles to provide a tab to facilitate removal of the carrier from the dressing in supporting a flexible film such as polyurethane film based adhesive dressings of the same order of size.

The carrier member used in the invention will usually be flexible to allow the dressing during the application thereof to bend but will be sufficiently stiff to provide support for the backing.

Other removable protectors which are opaque may include silicone coated release papers. Suitably the removable protector may have a weight per unit area of 100 to 140 gsm, and preferably 110 to 130 gsm, for example 120 gsm. The removable protector may be present as a single piece or may be divided into two or more pieces. If the protector is in a single piece then it is desirable that the stripping load of the support layer from the backing layer is greater than that of the protector from the adhesive otherwise there is a risk that the support layer would peel from the backing layer before the protector can be removed. Preferably the removable protector is in two pieces. The width of the removable protector when it extends beyond the edge of the backing layer may be less than the corresponding width of the support layer where it extends beyond the backing layer. This facilitates grasping the support layer in one hand and the protector in the other.

Aptly when the protector is in two pieces, one piece is significantly larger than the other. The smaller piece may be V-shaped with the apex of the V in the interior of the dressing. The larger piece of the removable protector then covers the remaining adhesive surface and overlaps onto the V-shaped piece. In use the support layer and the V-shaped piece are gripped in one hand and the adhesive protector peeled off with the other. Alternatively only the V-shaped piece may be gripped. When the major portion of the dressing is in place the V-shaped piece may be removed and the remainder of the dressing applied to the patient. Then if desired the support layer is removed. Alternatively, if desired, the conformability of the dressing may be increased by removing the V-shaped piece first and the dressing handled aseptically by the projecting edges of the support layer.

Adhesive dressing may be prepared by casting a solution of the polymer which is to from the backing layer onto a long strip of the film which is to form the support layer. An adhesive may be cast or transfer coated onto the backing layer. The backing layer and adhesive layer may then be trimmed to the correct width on the support layer. The removable protector may then be applied to the adhesive surface in one or two pieces as described herein before. The material so formed may be further trimmed and then cut transversely to to form dressing of the appropriate size. The dressings may have an equivalent to $5 \times 5$ cm to $20 \times 20$ cm, for example $5 \times 7.5$ cm, $7.5 \times 10$ cm, $10 \times 14$ cm.

The adhesive dressing may be placed in a bacteria-proof pack, sealed and sterilized by conventional methods including using ethylene oxide or $\gamma$-irradiation.

Moisture vapor permeable dressings of the invention can suitably have a moisture vapor transmission rate of at least 300 g/m$^2$/24 h, more suitably at least 500 g/m$^2$/24 h at 37° C. at 100% to 10% relative humidity difference. The moisture vapor transmission rate of an adhesive dressing can be readily determined by the Payne Cup Method (in the upright position) described in European Patent No. 46071.

The wound dressing system of the invention can comprise a pack for the wound dressing or wound dressing assembly.

In a further embodiment of the invention the wound dressing system comprises a pack for the wound dressing which has a transparent or translucent panel and wherein the reference marks are on the panel.

The translucent or transparent panel can conveniently be part of pouch preferably a sterilizable pouch form of paper-film or film-film heat sealed laminate. Suitable pouches ca be selected from those conventionally used in the art.

The wound dressing system of the invention can also comprise a translucent or transparent layer in the form of a sheet or film layer which is not part of the dressing or wrapping.

In a further embodiment of the invention the wound dressing system comprises a pack containing at least one wound dressing and a transparent or translucent sheet or film wherein the reference marks are on the film or the sheet. The wound dressing or dressings within the pack however may be individually wrapped or packaged.

A transparent or translucent layer having reference marks which forms part of or is separate within the pack of a wound dressing system of the invention can be used to the monitor size of the wound prior to and after removal of the dressing from the wound. Such a layer can advantageously be used to monitor the size of the wound after the application of more than one dressing. Furthermore a record of the progress of the wound can be stored for reference for example in the patients records.

The wound dressing or wound dressing assembly of the invention is preferably sterile within a bacteria-proof pack.

The reference marks on the transparent or translucent layer of the dressing assembly can suitably be a series of spaced points or lines which extend in at least one direction for example and preferably the length of the dressing and preferably also in the transverse direction for example on the width direction of the dressing, or dressing assembly.

The reference marks can conveniently be one or more linear scales, for example intersecting as a cross, a grid or a set of concentric circles or ellipses. The overall size of the reference marks and the distances between individual marks such as lines or dots can be adapted to the size of the dressing and the size of the wound intended to be treated by this dressing.

A grid of length 8 cm and width 10 cm with spacing of 5 mm between the lines of the grid have been found suitable for 14 cm$\times$10 cm dressings. Such reference marks can be printed onto the transparent or translucent layer by a conventional process.

It is preferred that the transparent or translucent layer is capable of being marked by a pen (including a ball point pen) or pencil to enable the size of the wound to be recorded. Comparison of two more of these records for the wound give an indication of the progress of the wound over the period when the records were taken.

The reference marks may be indexed with suitable letters or numbers to enable the size of the wound to be recorded without the necessity of storing the transparent or translucent layer.

Wound dressings of the invention are highly suitable for monitoring the size of ulcers and pressure sores.

The system may also comprise opaque components such as absorption pads or swabs which in use may be placed on top of the in situ dressing. Such opaque components are removed, without disturbing the dressing and the wound progress view through the in-situ dressing.

EXAMPLE 1

The present invention will now be illustrated by reference to the following examples and the accompanying dressings.

A rectangular wound dressing of the invention was prepared by adhering a carrier film to the handle strips of a wound dressing made in a similar manner to that of Example 1 of United Kingdom Application No. 2157955.

The wound dressing had a backing layer (100 mm$\times$100 mm) of polyurethane film (30 $\mu$m thick) which was coated with polyvinyl ethyl ether pressure sensitive adhesive (30 $\mu$m thick). The dressing had a pair of silicone coated paper handle strips (100 mm$\times$37 mm) which were attached adjacent to opposed edges of the backing layer by strips (100 mm$\times$25 mm) of tearable adhesive tape which cover marginal strips of the handle strips and the backing layer. The releasable protector (184$\times$100 mm) was a silicone release coated paper which covered the adhesive surface of dressing.

The carrier film (205 mm × 100 mm) was adhered to the handle strips by spaced apart (approx 150 mm) strips (10 mm wide) of pressure sensitive adhesive. The carrier film was a transparent polyethylene film 50 μm thick.

The outside surface of the polyethylene carrier film had reference marks in the form of a printed square grid (grid lines spaced 5 mm apart). The grid reference marks were on a 8 cm × 10 cm area of the carrier film covering the backing layer of the dressing and the grid lines were parallel to the sides or edges of the dressing.

In tests it was found that after application of the dressing to a wound an outline of the wound could be marked on the carrier film by a suitable marking pen. The carrier film was then removed, the size of the wound assessed by reference to the grid reference marks. The marked carrier film could then be stored for future reference for example comparison with a marked carrier film from a second dressing applied over the wound after the first dressing had been removed. Comparison of the two wound outlines would give an indication of the progress of the wound.

EXAMPLE 2

A dressing (20 cm × 30 cm) was made having the construction shown in the drawing which shows the dressing schematically in cross-section.

Figure 2:
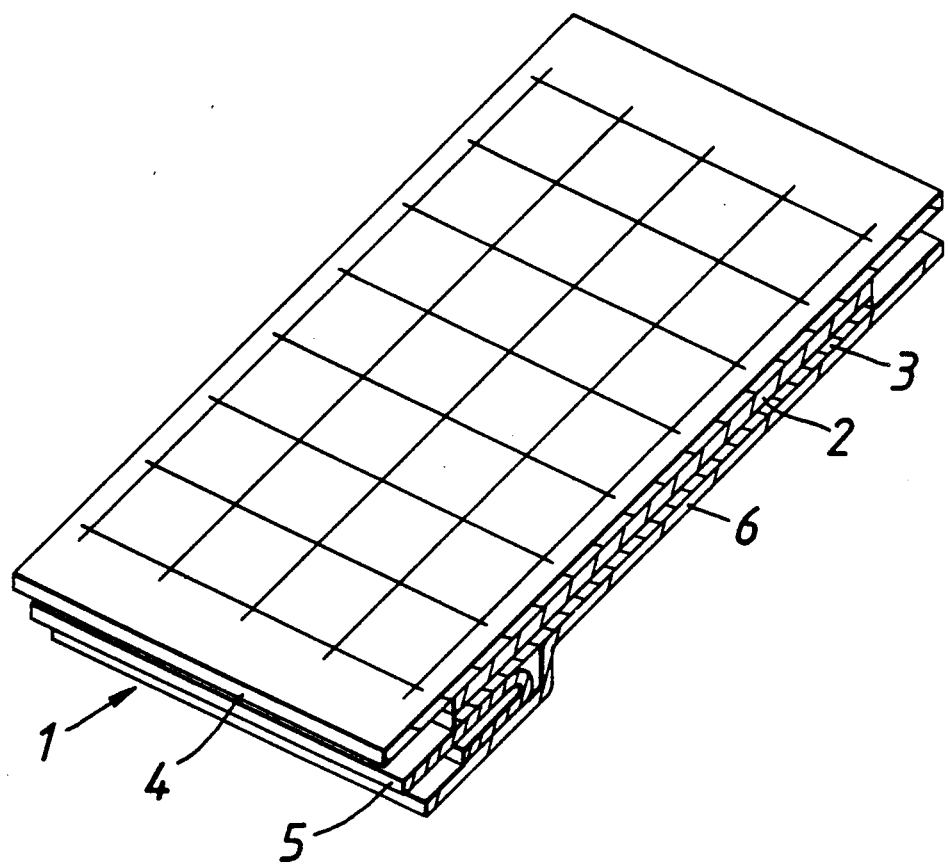

The adhesive dressing (1) as shown in FIGS. 1 and 2 comprises a backing layer (2) formed from a film of a polyether polyurethane. The film had a weight per unit area of 30 gsm and a thickness of 27.5 μm. The backing layer (2) had on one surface a pressure sensitive adhesive layer (3) formed by transfer coating a polyacrylate ester adhesive previously coated on a silicone treated release paper. The adhesive layer (3) had a weight per unit area of 30 gsm. On the non-adhesive surface of the backing layer (2) was a support layer (4). The support layer (4) comprised a laminate of polyethylene (20 gsm): polypropylene (20 gsm) having a 5 mm × 5 mm grid pattern printed on the polypropylene prior to lamination. One surface of the laminate was treated wit a siliconising agent.

The backing layer was formed by casting the polyether polyurethane onto the non-silicone surface of the laminate.

Covering the adhesive layer of the dressing was a removable protector, formed in two pieces (5, 6), the smaller piece (5) being folded in a V-shape. The larger protector (6) was essentially flat and overlapped the smaller one.

The dressing, for presentation to wound on the elbow was cut through with scissors, along lines shown on the support layer to form wings around a central operative area. The larger protector (6) was removed and the dressing placed on the bent elbow with the operative area covering the wound. The smaller protector (5) was removed and the support covered dressing smoothed down. The support (4) was then removed by picking up one of the non-bonded edges of the support. The dressing was smoothly adhered to the skin with no unsightly puckering of the dressing. On flexing the arm the dressing conformed with the relaxed skin in the elbow region.

I claim:

1. A wound dressing system comprising a translucent or transparent dressing and at least one further transparent or translucent layer having reference marks thereon for use in monitoring the wound wherein the dressing comprises a transparent or translucent elastomeric moisture vapor transmitting backing film coated on one surface thereof with a layer of a pressure sensitive adhesive.

2. A system as claimed in claim 1 wherein the adhesive layer is a discontinuous layer.

3. A system as claimed in claim 1 in which the dressing is impervious to liquid water and bacteria but is moisture vapor permeable.

4. A system as claimed in claim 3 in which the dressing has a moisture vapor transmission rate of not less than 300 gm m$^2$ 24 hr$^{-1}$ at 37° C. and a relative humidity difference of 10 to 100%.

5. A system as claimed in claim 1 in which the further layer is a protector sheet over the adhesive surface of the dressing.

6. A system as claimed in claim 1 in which the further layer is a panel of translucent or transparent material.

7. A system as claimed in claim 6 wherein the panel is part of a package for containing the dressing.

8. A system as claimed in claim 1 in which the further layer is removable carrier member for supporting the dressing.

9. A system as claimed in claim 8 in which the carrier layer is releasably bonded to at least part of the surface of the backing layer opposed to the adhesive coated surface.

10. A system as claimed in claim 8 in which the carrier layer is bonded to substantially the entire surface of the backing layer.

11. A system as claimed in claim 8 in which the carrier layer is bonded to the backing film at opposed edges thereof.

12. A system as claimed in claim 1 wherein the reference marks are in the form of a grid.

13. A dressing as claimed in claim 8 in which both the protector and support layers extend beyond the backing layer at two opposed edges.

14. An adhesive dressing comprising a backing layer having a pressure sensitive adhesive layer coated on one surface thereof, a removable protector covering the adhesive coated surface and extending beyond the backing layer at one or more edges thereof and a support layer removably attached to the surface of the backing layer opposed to the adhesive coated surface, the support layer extending beyond the backing layer at one or more of said edges and the support layer is a transparent polymeric film carrying reference markings.

15. A dressing as claimed in claim 14 wherein the reference marks are in the form of a grid.

16. A method of monitoring a wound covered with a transparent or translucent dressing which method comprises superposing a layer of transparent or translucent material bearing reference marks over the covered wound, and viewing the wound through the layer, at times during the period the wound is covered by the dressing.

* * * * *